US006881841B2

(12) United States Patent
Takeuchi et al.

(10) Patent No.: US 6,881,841 B2
(45) Date of Patent: Apr. 19, 2005

(54) DIBENZOSUBERANYL PIPERAZINE DERIVATIVES AND DRUG-RESISTANCE OVERCOMING AGENTS CONTAINING THE DERIVATIVES

(75) Inventors: Tsutomu Takeuchi, 3-21-6, Okamoto, Setagaya-ku, Tokyo 157-0076 (JP); Hiroaki Takayanagi, 2-4-32, Shinbori, Niiza-shi, Saitama 352-0032 (JP); Seiki Kobayashi, Kanagawa (JP); Yumiko Osa, Tokyo (JP); Yumiko Suzuki, Kanagawa (JP); Yoko Sato, Aomori (JP); Masakazu Sakaguchi, Kanagawa (JP); Yoshiyuki Miyata, Kanagawa (JP)

(73) Assignees: Tsutomu Takeuchi, Tokyo (JP); Hiroaki Takayanagi, Niiza (JP); Pola Chemical Industries, Inc., Shizuoka (JP)

(*) Notice: Subject to any disclaimer, the term of this patent is extended or adjusted under 35 U.S.C. 154(b) by 0 days.

(21) Appl. No.: 10/416,514

(22) PCT Filed: Nov. 20, 2001

(86) PCT No.: PCT/JP01/10128

§ 371 (c)(1),
(2), (4) Date: May 22, 2003

(87) PCT Pub. No.: WO02/42284

PCT Pub. Date: May 30, 2002

(65) Prior Publication Data

US 2004/0029895 A1 Feb. 12, 2004

(30) Foreign Application Priority Data

Nov. 22, 2000 (JP) ........................................ 2000-355393

(51) Int. Cl.$^7$ ............................................. C07D 295/00
(52) U.S. Cl. ...................................................... 544/381
(58) Field of Search .......................................... 544/381

(56) References Cited

U.S. PATENT DOCUMENTS 3,257,404 A  * 6/1966 Clement ...................... 544/381
5,225,411 A     7/1993 Regnier et al.

FOREIGN PATENT DOCUMENTS

| EP | 363212 | 4/1990 |
| JP | 04-134070 | 5/1992 |
| JP | 06-116240 | 4/1994 |
| JP | 06-199669 | 7/1994 |
| JP | 06-271556 | 9/1994 |
| JP | 2000-072612 | 3/2000 |
| WO | 88/03802 | 6/1988 |
| WO | 92/18131 | 10/1992 |
| WO | 94/22842 | 10/1994 |
| WO | 94/22846 | 10/1994 |
| WO | 95/10516 | 4/1995 |

OTHER PUBLICATIONS

David F. Tang–Wai et al.: "Human (MDR1) and mouse (mdr1, mdr3) P–glycoproteins can be distinguished by their respective drug resistance profiles and sensitivity to modulators" Biochemistry, vol. 34, No. 1, pp. 32–39, 1995.

* cited by examiner

Primary Examiner—Alton Pryor
(74) Attorney, Agent, or Firm—Oblon, Spivak, McClelland, Maier & Neustadt, P.C.

(57) ABSTRACT

Dibenzosuberanyl piperazine derivatives represented by the following formula (I):

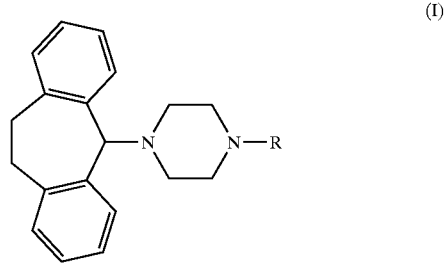

wherein R represents an aliphatic hydrocarbon group, which may contain one or more heteroatom-containing substituent groups and may preferably contain 2 to 30 carbon atoms, and physiologically acceptable salts thereof; and medicinal compositions containing these dibenzosuberanyl piperazine derivatives and/or physiologically acceptable salts thereof.

These compounds show effectiveness in allowing resistance-acquired causes of diseases to restore sensitivity to drug, that is, a resistance overcoming effect.

14 Claims, No Drawings

DIBENZOSUBERANYL PIPERAZINE DERIVATIVES AND DRUG-RESISTANCE OVERCOMING AGENTS CONTAINING THE DERIVATIVES

TECHNICAL FIELD

This invention relates to novel dibenzosuberanyl piperazine derivatives and salts thereof, which are useful for the treatment of drug-resistant diseases, and also to medicinal compositions containing these compounds as active ingredients.

BACKGROUND ART

Chemotherapy was once assumed to be highly useful as a method for treating infectious diseases and cancers, and it was also hoped that many infectious diseases would be overcome and even complete cure of cancers would no longer be a dream. Examples of such infectious diseases include tuberculosis that was once accounted as one of the mortal diseases, and other diseases, such as yellow fever, dengue fever, malaria and leishmaniasis, that have hampered the progress of many countries in tropical region. In recent years, drug-resistant strains are emerging against such chemotherapies. In other words, there are rapid increases of the strains that are hardly affected by any classical medicines thought before to be effective. Moreover, such strains are strongly resistant not only against the medicines to which they were already exposed, but also against those to which they have not yet been exposed. As a result, once infected by these strains, the patient infected is no longer able to have any therapeutic means, so there is a great concern about the re-outbreak of diseases which were thought to have already disappeared. Emergence of such strains is actually recognized in the chemotherapy of cancer, and there are many instances showing the phenomenon that the effect of chemotherapeutic agents on cancers could be sharply lowered when used for the treatment of recurrent cancers. The mechanism of this phenomenon proved to be associated with the action of ABC-dependant pumps (ABC pumps). Also, these resistant cancers and resistant germs were found to have plenty of similarity in their gene structure of ABC pumps, suggesting that there is extremely clsoe correlation between them.

For causes of diseases, said causes having such drug resistance, dibenzosuberanyl piperazines of the below-described formula (II) in which $R^1$ is a hydrogen atom and $R^2$ is an aromatic oxy(or thio)hydrocarbon group are known to have effectiveness in overcoming such drug resistance, in other words, when administered together with drug, to act such that the causes of diseases are enhanced in their sensitivity to the drug. Despite such an effect, however, their sensitivity may not be restored to levels as high as the sensitivity of their corresponding non-resistant strains in some instances, leading to a desire for the development of a substance having a still stronger drug-resistance overcoming effect, namely, a substance excellent in the effect of allowing resistance-acquired causes of diseases to restore their sensitivity to drug.

An object of the present invention is, therefore, to provide a substance excellent in the effect of allowing a resistance-acquired cause of disease to restore its sensitivity to drug, that is, in resistance overcoming effect.

DISCLOSURE OF THE INVENTION

With the foregoing circumstances in view, the present inventors have enthusiastically proceeded with intensive research in pursuit of substances having a still stronger drug-resistance overcoming effect. As a result, a strong drug-resistance overcoming effect has been found to exist in dibenzosuberanyl piperazine derivatives represented by the below-described formula (I), leading to the completion of the present invention.

Specifically, the present invention provides a dibenzosuberanyl piperazine derivative represented by the following formula (I):

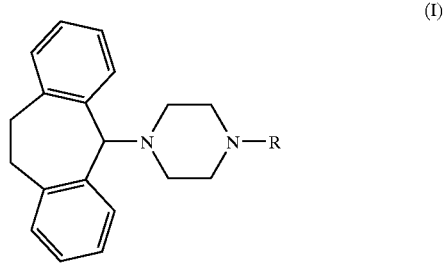

wherein R represents an aliphatic hydrocarbon group which may contain one or more heteroatom-containing substituent groups, or a physiologically acceptable salt thereof (physiologically acceptable salt).

The present invention also provides a medicinal composition, especially a medicinal composition for overcoming drug resistance of a hazardous microorganism, which comprises one or more compounds or salts selected from dibenzosuberanyl piperazine derivatives represented by the formula (I) and physiologically acceptable salts thereof.

The present invention further provides use of one or more compounds or salts, which are selected from dibenzosuberanyl piperazine derivatives represented by the formula (I) and physiologically acceptable salts thereof, for the production of a drug, especially a drug for overcoming drug resistance of a hazardous microorganism.

The present invention still further provides a method for overcoming drug resistance of a hazardous microorganism, which comprises administering an effective amount of one or more compounds or salts selected from dibenzosuberanyl piperazine derivatives represented by the formula (I) and physiologically acceptable salts thereof.

BEST MODES FOR CARRYING OUT THE INVENTION

Each compound according to the present invention has a structure represented by the formula (I). The aliphatic hydrocarbon group represented by R in the formula. (I) preferably has a linear or branched structure of 2 to 30, preferably 3 to 20, especially preferably 3 to 10 carbon atoms. Further, among such aliphatic hydrocarbon groups, those containing one or more, preferably one or two double and/or triple bonds are preferred. Such aliphatic hydrocarbon groups may each contain up to five, preferably up to two heteroatom-containing substituent groups. Examples of heteroatoms can include oxygen, nitrogen, sulfur and phosphorus atoms. Of these, oxygen atom is preferred. As the heteroatom-containing substituent groups, hydroxyl, acyl and acyloxy groups, especially hydroxyl, $C_{1-4}$ acyl and $C_{1-4}$ acyloxy groups are preferred, with hydroxyl and $C_{1-4}$ acyl groups being more preferred.

Those particularly preferred among the compounds represented by the formula (I) are compounds represented by the following formula (II):

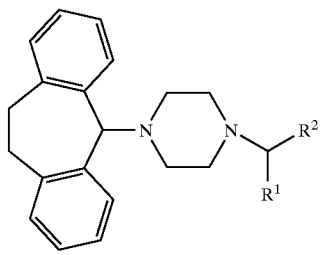
(II)

wherein $R^1$ is a hydrogen atom or a $C_{1-4}$ alkyl group which may contain one or more hydroxyl groups, $C_{1-4}$ acyl groups or $C_{1-4}$ acyloxy groups; and $R^2$ is a $C_{2-30}$ aliphatic hydrocarbon group which may contain one or more $C_{1-4}$ acyl groups, $C_{1-4}$ acyloxy groups and/or hydroxyl groups.

Examples of the $C_{1-4}$ alkyl group represented by $R^1$ can include methyl, ethyl, propyl, isopropyl, butyl, isobutyl, sec-butyl, and tert-butyl. Examples of the substituent groups on the alkyl group can include $C_{1-4}$ acyl groups such as acetyl and propionyl; $C_{1-4}$ acyloxy groups such as acetoxy and propionyloxy; and hydroxyl.

Preferred as $R^2$ are aliphatic hydrocarbon groups which have a linear or branched structure and contain 2 to 30, preferably 2 to 20, especially preferably 2 to 10 carbon atoms. Among these, those having one or two double and/or triple bonds are particularly preferred. These aliphatic hydrocarbon groups may each contain one or more substituent groups such as $C_{1-4}$ acyl groups, $C_{1-4}$ acyloxy groups and/or hydroxyl groups. Illustrative of these acyl groups and acyloxy groups can be the same as those which can substitute on the alkyl group represented by $R^1$. Preferably, at least one of $R^1$ and $R^2$ contains one or more hydroxyl groups, acyl groups or acyloxy groups.

As particularly preferred compounds among the compounds according to the present invention represented by the formula (I) or the formula (II), the following compounds can be exemplified:

1-Dibenzosuberanyl-4-(2-hydroxydecan-9-en-1-yl) piperazine (Compound 1) represented by the following formula:

Compound 1

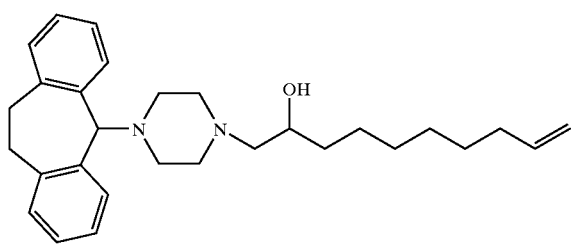

1-Dibenzosuberanyl-4-(2-hydroxy-7-octenyl)-piperazine (Compound 2) represented by the following formula:

Compound 2

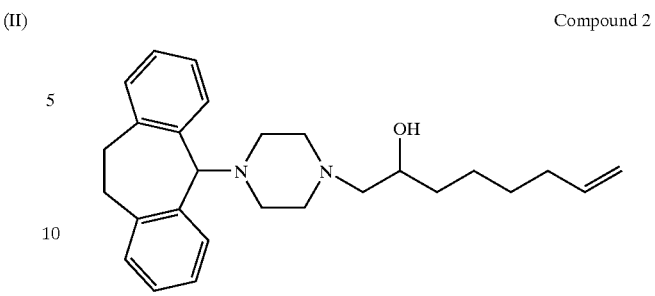

1-Dibenzosuberanyl-4-(2-hydroxy-5-hexenyl)-piperazine (Compound 3) represented by the following formula:

Compound 3

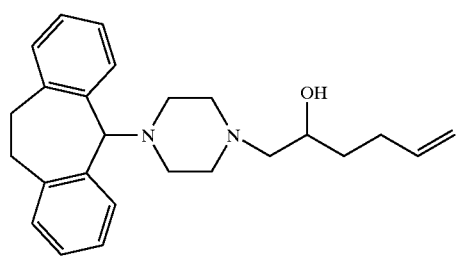

1-Dibenzosuberanyl-4-(2-hydroxy-3-butenyl)-piperazine (Compound 4) represented by the following formula:

Compound 4

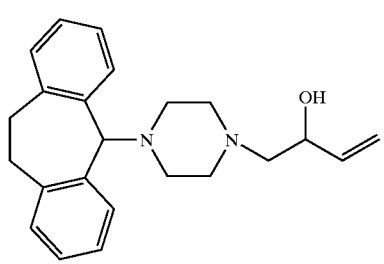

1-Dibenzosuberanyl-4-(1-hydroxybutan-3-en-2-yl) piperazine (Compound 5) represented by the following formula:

Compound 5

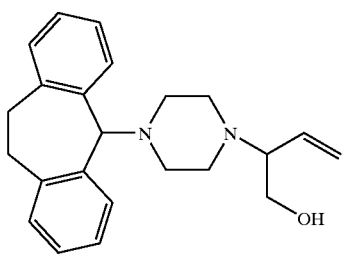

1-Dibenzosuberanyl-4-(4-hydroxy-2-butynyl)-piperazine (Compound 6) represented by the following formula:

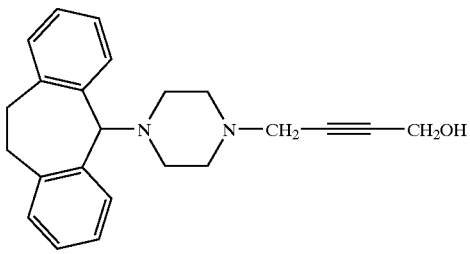

1-Dibenzosuberanyl-4-(4-acetoxy-2-butynyl)-piperazine (Compound 7) represented by the following formula:

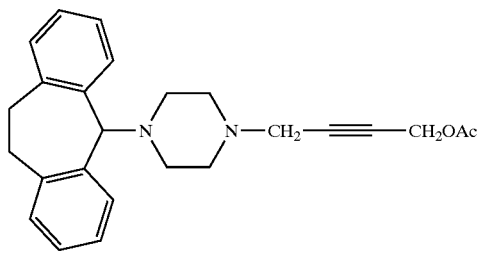

1-Dibenzosuberanyl-4-(2-hydroxydecanyl)piperazine (Compound 8) represented by the following formula:

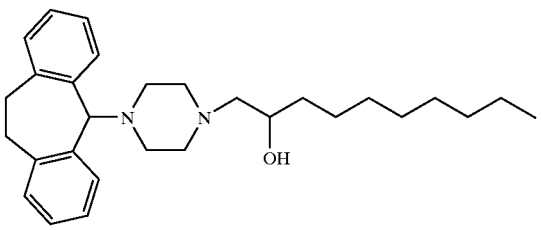

The compounds of the formula (I) or (II) can each be produced, for example, as illustrated by the following process A or process B:

Process A: Dibenzosuberanyl chloride and piperazine, which are both available on the market, are subjected to condensation in the presence of an alkali to obtain dibenzosberanyl piperazine, which is then subjected to ring-opening condensation with an aliphatic epoxide which has been obtained by oxidizing an aliphatic hydrocarbon.

Process B: The above-described dibenzosuberanyl piperazine and a chloride—which has been obtained by treating a polyol, the hydroxyl groups of which were protected except for one hydroxyl group, with a halogenating agent such as thionyl chloride—are subjected to condensation in the presence of an alkali, followed by deprotection.

In each of the process A and the process B, the reaction temperature of the ring-opening condensation reaction or condensation reaction may preferably be around room temperature. The reaction time may range from several hours to 24 hours or so, although it varies depending on the reaction temperature.

The compounds according to the present invention can be used as salts by treating them with acids. Illustrative of usable, physiologically acceptable salts are mineral acid salts such as the carbonates, hydrochlorides, sulfates, nitrates and phosphates; and organic acid salts such as the citrates and oxalates, with the carbonates being particularly preferred.

For hazardous germs which have acquired resistance to antimicrobial agents for hazardous microorganisms such as methicillin-resistant *Staphylococcus aureus* (MRSA), vancomycin-resistance *Euterococci* (VRE), resistant tubercle bacillus, resistant *Escherichia coli*, resistant plasmodium and resistant *Leishmania*, the compounds and/or salts according to the present invention are effective in lowering their resistance to drug. When each compound and/or salt according to the present invention is administered together with a chemotherapeutic agent, the drug resistance of the resistant microorganisms is lowered so that, even with a chemotherapeutic agent which did not work before, its effect can be exhibited. Illustrative of drugs the sensitivity to which is restorable as described above are antimalarials such as chloroquine and mefloquine; antiprotozoals such as anti-*leishmania* drugs like antimony-containing drugs; penicillin antibiotics, cephalosporin and cephalosporol antibiotics, new quinolone antibiotics, aminoglycoside antibiotics, and peptide antibiotics; tuberculostatics such as rifampin and streptomycin; and anticancer agents such as adriamycin, mitomycin, cisplatin and 5FU. With respect all of these drugs, drug-resistant strains have emerged. Verapamil and tricyclic compounds, despite their recognized drug resistance lowering effect, were not put to practical use because primary medicinal activities are developed before they exhibit an effect of lowering resistance to drug. As the compounds according to the present invention do no have any calcium antagonism, antidepressant effect or hypnotic effect, they develop no side effect in a resistance-overcoming-effect developing range.

Each medicinal composition according to the present invention contains the above-described compound and/or salt as an active ingredient. As no particular limitation is imposed on the administration route for the compound of the present invention, the medicinal composition according to the present invention can be used in any preparation form without any particular limitation insofar as the preparation form is of a conventionally-known type. Therefore, preparation forms such as a powder, granules, tablets, capsules, a solution, a lyophilized preparation, an oil-based gel preparation and a water-based gel preparation are all usable. Granules, tablets and capsules can be coated, so that a water-soluble resin such as hydroxypropylcellulose, enteric coating of hydroxypropylmethylcellulose, shellac or "EUDRAGIT" or sugar coating can be applied. For the formulation into such preparation forms, it is possible to incorporate, in addition to the compound or salt according to the present invention, one or more optional ingredients which are commonly used for the formulation into medicinal preparation forms. Examples of such optional ingredients can include excipients, binders, disintegrators, colorants, correctives, dispersants, emulsifiers, stabilizers, pH adjusters, and isotonicities. The medicinal composition according to the present invention can be produced by processing these active ingredient and optional ingredients by a method known per se in the art. The medicinal composition of the present invention is suited for medically obtaining the resistance overcoming effect of the compound or salt according to the present invention. It is, however, to be noted that, insofar as the compound or salt according to the present invention is used as an active ingredient, its use in the form of a medicinal composition for a medicinal activity other than the resistance overcoming effect shall also fall within the technical scope of the medicinal composition according to the present invention.

When the compound according to the present invention is used to overcome resistance, no particular limitation is imposed on its administration route. Illustrative administration routes can include oral administration, intravenous injection, intra-arterial injection, intraperitoneal injection, drip administration, and suppository-dependent intrarectal administration, although oral administration or intrarectal administration is preferred. The preferred dosage of the compound and/or salt according to the present invention, which is suited for the development of the above-described resistance overcoming effect, differs depending on the form of the preparation, but it is generally preferred to administer 10 to 1,000 mg, preferably 5 to 500 mg in one to several portions per adult (body weight: 60 kg) and day.

EXAMPLES

The present invention will hereinafter be described in further detail on the basis of Examples, although the present invention shall by no means be limited only to the following Examples.

Example 1

Preparation of 1-dibenzosuberanyl-4-(2-hydroxydecan-9-en-1-yl)piperazine (Compound 1)

Piperazine and dibenzosuberanyl chloride were reacted at 1:1 to obtain dibenzosuberanyl piperazine. That dibenzosuberanyl piperazine (1 parts by weight) and 1,2-epoxydecan-9-ene (2 parts by weight), subsequent to addition of molecular sieve 4 Å, were dissolved in methanol (100 parts by weight), and 1,5-diazobicyclo[5,4,0]undeca-5-ene (hereinafter abbreviated as "DBU") (0.5 part by weight) was added, followed by reflux for 1 hour. After the solvent was distilled off, the residue was purified by chromatography on a silica gel column (eluent: n-hexane:ethyl acetate=10:1→chloroform:methanol=10:1) to yield the title Compound 1 (0.7 part by weight, yield: 29.1%). Its instrumental analysis data are shown below.

MS(FAB): m/z 432 (M)$^+$. $^1$H-NMR (400 MHz, CDCl$_3$)δ: 1.25–1.50 (8H, broad, H-7', 4', 5', 6', 3'), 2.04 (2H, m, H-8'), 2.22 (1H, dd, H-1'a), 2.26 (1H, dd, H-1'b), 2.29–2.70 (8H, broad, H-12, 14, 13, 15), 2.80 (2H, ddd, H-10a, 11a), 3.61 (1H, qd, H-2'), 3.97 (1H, s, H-5), 4.00 (2H, ddd, H-10b, 11b), 4.93 (1H, qd, H-10a'), 4.99 (1H, qd, H-10'b), 5.81 (1H, qd, H-9'), 7.04–7.20 (8H, benzene); $^{13}$C-NMR(100 MHz, CDCl$_3$)δ: 25.53 (C-3'), 28.82 (C-7'), 29.02 (C-5'), 29.61 (C-6'), 31.69 (C-10, 11), 33.75 (C-8'), 34.89 (C-4'), 51.95, 53.5 (N-CH$_2$), 64.05 (C-1'), 66.06 (C-2'), 79.02 (C-5), 114.11 (C-10'), 139.59 (C-9'), 125.42, 127.63, 130.67, 139.12, 139.21, 139.24 (benzene).

Example 2

Preparation of 1-dibenzosuberanyl-4-(2-hydroxy-7-octenyl)piperazine (Compound 2)

The procedure of Example 1 was repeated likewise except for the replacement of 2-epoxydecan-9-ene with 1,2-epoxy-7-octene to yield the title Compound 2 (0.7 part by weight, yield: 18.0%). Its instrumental analysis data are shown below.

MS(FAB): m/z 404 (M)$^+$. $^1$H-NMR(400 MHz, CDCl$_3$)δ: 1.30–1.50 (6H, broad, H-4', 5', 3'), 2.04 (2H, broad, H-6'), 2.44 (2H, broad, H-1'), 2.46–2.70 (8H, broad, H-12, 13, 14, 15), 2.80 (2H, ddd, H-10a, 11a), 3.80 (2H, broad, H-2'), 3.95 (2H, ddd, H-10b, 11b), 4.03 (1H, s, H-5), 4.93 (1H, qd, H-8'a), 4.98(1H, qd, H-8'b), 5.79 (1H, qd, H-7'), 7.04–7.20 (8H,benzene); $^{13}$C-NMR(100 MHz, CDCl$_3$)δ: 24.93 (C-4'), 28.87 (C-5'), 31.75 (C-10, 11), 33.61 (C-6'), 34.76 (C-3'), 50.43, 53.88 (N-CH$_2$), 64.15 (C-1'), 65.68 (C-2'), 78.49 (C-5), 114.39 (C-8'), 139.55 (C-7'), 125.63, 127.89, 130.73, 130.89, 138.44, 138.75 (benzene).

Example 3

Preparation of 1-dibenzosuberanyl-4-(2-hydroxy-5-hexenyl)piperazine (Compound 3)

The procedure of Example 1 was repeated likewise except that 1,2-epoxydecan-9-ene was replaced with 1,2-epoxy-5-hexene, DBU was replaced with triethylamine, and the residue was purified by chromatography on a silica gel column (eluent: chloroform:methanol=10:1), yielding the title Compound 3 (0.9 part by weight, yield: 48.4%). Its instrumental analysis data are shown below.

Mass spectrum (EI): m/z 376 (M)$^+$. MS(EI): m/z 376 (M)$^+$. $^1$H-NMR(300 MHz, CDCl$_3$)δ:1.47 (2H, m, H-3'), 2.16 (2H, m, H-4'), 2.37 (2H, m, H-1'), 2.3–2.70 (8H, broad, H-12 to 15), 2.79 (2H, ddd, H-10a, 11a), 3.64 (2H, qd, H-2'), 3.96 (1H, s, H-5), 3.99 (2H, ddd, H-10b, 11b), 4.94 (1H, qd, H-6'a), 5.02 (1H, qd, H-6'b), 5.82 (1H, m, H-5'), 7.03–7.20 (benzene); $^{13}$C-NMR(75 MHz, CDCl$_3$)δ: 29.84 (C-4'), 31.72 (C-10, 11), 34.07 (C-3'), 51.69, 53.48, 53.45 (N-CH$_2$), 63.92 (C-1'), 65.52 (C-2'), 79.03 (C-5), 114.58 (C-6'), 138.48 (C-5'), 126.45, 127.66, 130.70 (benzene).

Example 4

Preparation of 1-dibenzosuberanyl-4-(2-hydroxy-3-butenyl)piperazine (Compound 4) and 1-dibenzosuberanyl-4-(1-hydroxybutan-3-en-2-yl)-piperazine (Compound 5)

The procedure of Example 1 was repeated likewise except for the replacement of 1,2-epoxydecan-9-ene with 1,2-epoxy-3-butene to yield a mixture of the title Compound 4 and the title Compound 5. Further, the mixture was purified by chromatography on a silica gel column (eluent: n-hexane:ethyl acetate=1:1→1:2) to yield the title Compound 4 (0.6 part by weight, yield: 37.2%) and the title Compound 5 (0.25 part by weight, yield: 17.3%). Their instrumental analysis data are shown below.

Compound 4

MS(EI): m/z 348 (M-H)$^+$. $^1$H-NMR(600 MHz, CDCl$_3$)δ: 2.29–2.64 (8H, broad, H-12, 13, 14, 15), 2.36 (2H, td, H-1'a, H-1'b), 2.79, 2.80 (2H, ddd, H-10a, 11a), 3.97 (1H, s, H-5), 3.99, 4.00 (2H, ddd, H-10b, 11b), 4.11 (1H, qd, H-2'), 5.13 (1H, qd, H-4'a), 5.31 (1H, qd, H-4'b), 5.75 (1H, qd, H-3'), 7.05–7.18 (benzene); $^{13}$C-NMR(75 MHz, CDCl$_3$)δ: 31.72, 31.74 (C-10, 11), 51.90, 53.42 (N-CH$_2$), 63.53 (C-1'), 67.65 (C-2'), 79.04 (C-5), 115.74 (C-4'), 138.41 (C-3'), 125.46, 127.69, 130.71, 139.19, 139.61 (benzene). mp 93° C.

Compound 5

MS(EI):m/z 348(M-H)$^+$. $^1$H-NMR(300 MHz, CDCl$_3$)δ: 2.22–2.66 (8H, broad, H-12, 13, 14, 15), 2.76, 2.82 (2H, ddd, H-10a, 11a), 3.05 (1H, qd, H-2'), 3.49, 3.51 (2H, dd, H-1'a, H-1'b), 3.96 (1H, s, H-5), 3.98, 4.00 (2H, ddd, H-10b, 11b), 5.15 (1H, qd, H-4'b), 5.25 (1H, qd, H-4'a), 5.72 (1H, qd, H-3'), 7.00–7.40 (benzene); $^{13}$C-NMR(100 MHz, CDCl$_3$)δ: 1.74 (C-10, 11), 52.22 (N-CH$_2$), 60.38 (C-1'), 68.17 (C-2'), 79.07 (C-5), 119.63 (C-4'), 133.07 (C-3'), 125.43, 127.66, 130.68, 139.22, 139.60, 139.64 (benzene). mp 123° C.

Example 5

Preparation of 1-dibenzosuberanyl-4-(4-hydroxy-2-butynyl)piperazine (Compound 6) and 1-dibenzosuberanyl-4-(4-acetoxy-2-butynyl)-piperazine (Compound 7)

1,4-Butynediol (10 parts by weight) was dissolved in pyridine (200 parts by weight), and under ice cooling, acetic anhydride (20 parts by weight) was added dropwise. Subsequent to a reaction for 2 hours, the reaction mixture was concentrated under reduced pressure. The residue was purified by chromatography on a silica gel column (eluent: chloroform:ethyl acetate=1:1) to yield monoacetin. Monoacetin (14 parts by weight) was dissolved in anhydrous benzene (20 parts by weight), and the thus-obtained solution was added dropwise to an anhydrous benzene solution in which pyridine and thionyl chloride (17 parts by weight) had been dissolved. After the mixture was heated overnight at 60° C., the mixture was subjected to liquid-liquid extraction with equiamounts of water and dichloromethane. The dichloromethane layer was collected and concentrated to afford reaction products. Separately, dibenzosuberanyl piperazine (14 parts by weight) was dissolved in dimethylformamide (100 parts by weight). To the solution so obtained, a solution of the reaction products in DBU (14 parts by weight) and dimethylformamide was added dropwise, followed by overnight stirring at room temperature. Subsequent to concentration of the reaction mixture, the residue was subjected to liquid-liquid extraction with equiamounts of chloroform and water. The chloroform layer was collected, and subsequent to concentration, the residue was purified by chromatography on a silica gel column (eluent: toluene:ethyl acetate=2:1) to yield Compound 7 (17.3 parts by weight, yield: 65.3%). One part by weight of Compound 7 was dissolved in methanol (20 parts by weight), and subsequent to addition of potassium carbonate (5.8 parts by weight), the resulting mixture was stirred overnight at room temperature. The reaction mixture was filtered. After the solvent was distilled off, the residue was purified by chromatography on a silica gel column (eluent: chloroform:methanol=10:1) to yield Compound 6 (0.6 part by weight, yield: 85.9%). Their instrumental analysis data will be shown next.

Compound 6

MS(FAB): m/z 347 (M+H)$^+$, 369(M+Na)$^+$. $^1$H-NMR(600 MHz, CDCl$_3$)δ: 2.3–2.60 (8H, broad, H-12 to 15), 2.78, 2.80 (2H, ddd, H-10a, 11a), 3.26 (2H, dd, N—CH$_2$C=), 3.96 (1H, s, H-5), 3.99, 4.00 (2H, ddd, H-10b, 11b), 4.26 (2H, dd, C=C—CH$_2$—OH), 7.06, 7.11, 7.16 (8H, benzene); $^{13}$C-NMR(150 MHz, CDCl$_3$)δ: 31.76 (C-10,11), 47.04 (N—CH$_2$C=), 51.15, 52.54 (N—CH$_2$), 51.69 (C—CH$_2$OH), 79.05 (C=C—CH$_2$—OH), 81.08 (C-5), 83.25 (N—CH$_2$C=), 125.43, 127.67, 130.69, 130.75, 139.19, 139.67 (benzene). mp 129° C.

Compound 7

MS(FAB): m/z 388(M)$^+$. $^1$H-NMR(600 MHz, CDCl$_3$)δ: 2.08 (3H, s, OAc), 2.3–2.60 (8H, broad, H-12 to 15), 2.79, 2.80 (2H, ddd, H-10a, 11a), 3.28 (2H, dd, N—CH$_2$C=), 3.97 (1H, s, H-5), 4.00, 4.01 (2H, ddd, H-10b, 11b), 4.68 (2H, dd, C=C—CH$_2$—OAc), 7.0–7.20 (8H, benzene); $^{13}$C-NMR(150 MHz, CDCl$_3$)δ: 20.69 (CH$_3$CO), 31.73 (C-10, 11), 46.97 (N—CH$_2$C=), 51.69, 52.40 (N—CH$_2$), 52.43 (C—CH$_2$OAc), 78.88 (C=C—CH$_2$—OAc), 79.02 (C-5), 82.15 (N—CH$_2$C=), 125.40, 127.65, 130.67, 130.73, 139.18, 139.65 (benzene), 170.18 (C=O)

Example 6

Preparation of the hydrochloride of 1-dibenzosuberanyl-4-(2-hydroxy-3-butenyl)piperazine (Compound 4)

Compound 4 (1 part by weight) was dissolved in diethyl ether (30 parts by weight), to which HCl-saturated diethyl ether (2 parts by weight) was added to have Compound 4 precipitated as its hydrochloride. The precipitate was recrystallized from a mixed solvent of chloroform and ethyl acetate to yield the hydrochloride of Compound 4.

Example 7

Preparation of 1-dibenzosuberanyl-4-(2-hydroxydecanyl)piperazine (Compound 8)

To a solution of dibenzosuberanyl piperazine (139 mg, 0.5 mmol) in methanol (3 mL), 1,2-epoxydecane (0.13 mL, 1 mmol) and triethylamine (0.018 mL, 0.25 mmol) were added, followed by stirring for 24 hours. After the reaction mixture was concentrated, the residue was isolated and purified by chromatography on a silica gel column (chloroform:methanol=10:1) to yield Compound 8 as a pale yellow oil (81 mg, 37.3%).

MS (FAB): m/z 433(M−H)$^+$, 457(M+Na)$^+$. $^1$H-NMR(300 MHz, CDCl$_3$)δ: 0.9 (3H, t, CH$_3$), 1.2–1.5 (12H, broad, H-4',5',6',7',8',9'), 2.2–2.3 (8H, m, H-1',3'), 2.3–2.7 (8H, broad, H-12,14,13,15), 2.8 (2H, ddd, H-10a,11a), 3.6 (1H, dddd, H-2'), 3.9 (1H, s, H-5), 4.00 (2H, ddd, H-10b,11b), 7.04–7.20 (8H, benzene).

Example 8

Production Example of Preparation

Following the below-described formulation, granules were produced. Described specifically, the ingredients (a) were charged in a "NEW MARUMERIZER", and subsequent to mixing in a forced-air atmosphere, the ingredients (b) were sprayed while performing granulation. The resulting wet granules were dried at 37° C. for 12 hours in a forced-air atmosphere to afford granules.

| a) | Compound 4 | 30 parts by weight |
|---|---|---|
|  | Crystalline cellulose | 30 parts by weight |
|  | Lactose | 25 parts by weight |
|  | Hydroxypropylcellulose | 10 parts by weight |
| b) | Dilute ethanol (50%) | 195 parts by weight |
|  | Hydroxypropylcellulose | 5 parts by weight |

Test 1

With respect to Compounds 1 to 7, these invention compounds were tested for their resistance overcoming effect in an in vivo test making use of a chloroquine-resistant mouse malaria strain. The test was conducted following the following procedure.

Materials

Chloroquine-resistant malaria plasmodium *Plasmodlium chabaudi* (AS strain: chloroquine-resistant (3CQ)); and Mice: ICR male mice of 4–5 weeks old (20 to 25 g)

Method

1) Preparation of the compounds: Each test compound was dissolved beforehand in ¹⁄₁₀ volume of DMSO such that the dose of the compound to each mouse per administration would become a final concentration of 50 mg/kg/0.2 mL. The resulting solution was diluted with 0.85% physiological saline to provide a 10% DMSO suspension.

2) Inoculation with the chloroquine-resistant malaria plasmodium, *Plasmodium chabaudi* (AS strain: chloroquine-resistant (3CQ): Parasitized red blood cells (PRBCs) (5×10$^6$ (the 6$^{th}$ power of 10) cells/0.2 mL) were also prepared with 0.85% physiological saline, and inoculated through the caudal vein of each mouse with a 26×½-gauge tuberculin needle.

3) Administration of the compounds and chloroquine: Two hours after the inoculation with the plasmodium, each test compound (50 mg/kg/0.2 mL) was intraperitoneally administered with 21×½-gauge needles to three groups of mice per compound. Chloroquine solutions of three concentrations, which had been prepared with 0.85% physiological saline to give final concentrations of 0 mg/kg/0.1 mL, 2 mg/kg/0.1 mL and 3 mg/kg/0.1 mL, respectively, were then also administered intraperitoneally with 26×½-gauge tuberculin needles to the three groups of mice which had been administered with the compound. To three control groups, the three chloroquine solutions were only administered, respectively. The compound and chloroquine were administered four times in total, that is, on the $0^{th}$, $1^{st}$, $2^{nd}$ and $3^{rd}$ days after the inoculation with the plasmodium.

4) Determination of effect: Every day after the inoculation with the plasmodium, the tail of each mouse was cut to a minimum at the tip thereof with scissors to cause bleeding, and a Giemsa staining specimen smeared with a thin film of the blood was prepared. On the $5^{th}$ day, the number of PRBCs per 10,000 red blood cells was counted, and based on a comparison of the PRBC number with the corresponding number of the group administered only with chloroquine, the chloroquine resistance overcoming effect of the test compound was determined. Test results are shown in Table 1.

TABLE 1

| Compound | Chloroquine 0 mg | Chloroquine 2 mg | Chloroquine 3 mg |
|---|---|---|---|
| Control | 5100 | 4900 | 3750 |
| Compound 1 | 4250 | 3100 | 280 |
| Compound 2 | 8450 | 0 | 0 |
| Compound 3 | 4500 | No tested | 292 |
| Compound 4 | 8000 | 430 | 0 |
| Compound 5 | Not tested | Not tested | 0 |

From the results in Table 1, it is understood that the compounds according to the present invention all lowered the resistance of the chloroquine-resistant plasmodium and increased its sensitivity to chloroquine.

Test 2

Resistance overcoming effect of Compound 8 was tested in a similar manner as in Test 1. The time of determination of the effect was set on the fourth day. The results are shown in Table 2.

TABLE 2

| Compound | Chloroquine 0 mg | Chloroquine 2 mg | Chloroquine 3 mg |
|---|---|---|---|
| Control | 4912 | 4525 | 3600 |
| Compound 8 | 7475 | 4875 | 3025 |

From Table 2, it is understood that the dosage response became clearer by the administration of Compound 8. This is attributed to overcoming of chloroquine resistance by Compound 8.

INDUSTRIAL APPLICABILITY

The compounds according to the present invention show effective in allowing causes of diseases, which have acquired resistance, to restore sensitivity to drug, namely, a resistance overcoming effect.

What is claimed is:

1. A dibenzosuberanyl piperazine compound represented by the following formula (I):

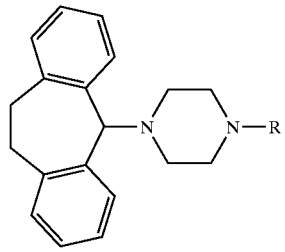

(I)

wherein R is an aliphatic hydrocarbon group containing i) one or more double bonds and/or triple bonds and ii) and a hydroxyl group; and wherein said aliphatic hydrocarbon group may contain one or more heteroatom-containing substituent groups, or a physiologically acceptable salt thereof.

2. The compound or the physiologically acceptable salt thereof as defined in claim 1, wherein each heteroatom forming R in the formula (I) is an oxygen atom.

3. The compound or the physiologically acceptable salt thereof as defined in claim 1 or 2, wherein R in the formula (I) is a $Cr_{2-30}$ aliphatic hydrocarbon group which may contain one or more substituent groups each of which is selected from a hydroxyl group, a $C_{1-4}$ acyl group or a $C_{1-9}$ acyloxy group.

4. The compound or the physiologically acceptable salt thereof as defined in claim 1 or 2, wherein R in the formula (I) is a $C_{2-30}$ unsaturated aliphatic hydrocarbon group, which contains one or more double and/or triple bonds and may contain one or more substituent groups each of which is selected from a hydroxyl group, a $C_{1-9}$ acyl group or a $C_{1-4}$ acyloxy group.

5. The compound or the physiologically acceptable salt thereof as defined in claim 1, wherein said compound represented by the formula (I) is a compound represented by the following formula (II):

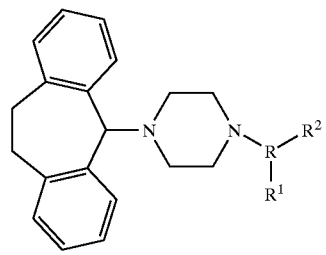

(II)

wherein $R^1$ represents a hydrogen atom or a $C_{1-4}$ alkyl group which may contain one or more hydroxyl groups, $C_{1-4}$ acyl groups or $C_{1-4}$ acyloxy groups; and $R^2$ represents a $C_{2-30}$ aliphatic hydrocarbon group which may contain one or more $C_{1-4}$ acyl groups, $C_{1-4}$ acyloxy groups and/or hydroxyl groups.

6. The compound or the physiologically acceptable salt as defined in claim 5, wherein $R^1$ in the formula (II) represents a hydrogen atom or a $C_{1-4}$ alkyl group which may contain one or more hydroxyl groups, $C_{1-4}$ acyl groups or $C_{1-4}$ acyloxy groups; and $R^2$ represents a $C_{2-30}$ unsaturated aliphatic hydrocarbon group which contains one or more double and/or triple bonds and may contain one or more $C_{1-4}$ acyl groups, $C_{1-4}$ acyloxy groups and/or hydroxyl groups.

7. The compound or the physiologically acceptable salt thereof as defined in claim 5, wherein in the formula (II), $R^1$ represents a hydrogen atom or a $C_{1-4}$ alkyl group which may contain one or more hydroxyl groups; and $R^2$ represents a $C_{2-10}$ unsaturated aliphatic hydrocarbon group which contains one or two double and/or triple bonds and may contain one or more hydroxyl groups and/or $C_{1-4}$ acyloxy groups.

8. The compound or the physiologically acceptable salt thereof as defined in claim 1, wherein said compound represented by the formula (I) is a compound selected from the group consisting of the following compounds:

1-dibenzosuberanyl-4-(4-hydroxydecan-9-en-1-yl) piperazine, 1-dibenzosuberanyl-4-(2-hydroxy-7-octenyl)piperazine, 1-dibenzosuberanyl-4-(2-hydroxy-5-hexenyl)piperazine, 1-dibenzosuberanyl-4-(2-hydroxy-3-butenyl)piperazine, 1-dibenzosuberanyl-4-(1-hydroxybutan-3-en-2-yl) piperazine, 1-dibenzosuberanyl-4-(4-hydroxy-2-butynyl)-piperazine, 1-dibenzosuberanyl-4-(4-acetoxy-2-butynyl)piperazine, and 1-dibenzosuberanyl-4-(2-hydroxydecanyl)piperazine.

9. A medicinal composition, comprising:
one or more compounds or salts selected from the group consisting of a compound and a physiologically acceptable salt thereof as defined in claim 1.

10. A method for overcoming drug resistance of a hazardous microorganism, which comprises:
administering an effective amount of one or more compounds or salts selected from the group consisting of compounds and physiologically acceptable salts thereof as defined in claim 1 to a subject in need thereof.

11. The method as defined in claim 10, wherein said hazardous microorganism is a plasmodium.

12. The method of claim 10, wherein said hazardous microorganism is methicillin-resistant *Staphylococcus aureus*, vancomycin-resistance *Euterococci*, resistant tubercle bacillus, resistant *Escherichia coli*, resistant *plasmodium* or resistant *Leishmania*.

13. The method of claim 10, further comprising:
administering a chemotherapeutic agent.

14. The compound of claim 1 or the physiologically acceptable salt thereof, which does not exhibit calcium antagonism, antidepressant effect or hypnotic effect.

* * * * *